United States Patent [19]

Tabacco et al.

[11] 4,407,962

[45] Oct. 4, 1983

[54] COMPOSITION FOR THE COLORIMETRIC DETERMINATION OF METALS

[75] Inventors: Alessandro Tabacco, Siena; Paolo Tarli, Monteriggioni, both of Italy

[73] Assignee: Istituto Sieroteropico E. Vaccinogeno Toscano "Sclavo" S.p.A., Siena, Italy

[21] Appl. No.: 215,176

[22] Filed: Dec. 11, 1980

[30] Foreign Application Priority Data

Feb. 26, 1980 [IT] Italy .................. 20177 A/80

[51] Int. Cl.³ .................. G01N 33/48; G01N 33/52
[52] U.S. Cl. .................. 436/74; 436/84; 422/61
[58] Field of Search .................. 252/408; 23/230 B; 422/61; 436/73, 84, 74

[56] References Cited

U.S. PATENT DOCUMENTS 4,224,034 9/1980 Denney et al. .................. 23/230 B
4,308,027 12/1981 Ceriotti .................. 23/230 B

OTHER PUBLICATIONS

Clinical Chemical Acta, vol. 114, pp. 287–290, (1981), Tabacco et al.

Clinical Chemical Acta, vol. 94, pp. 115–119, (1979), Garcic, A.

Microchemical Journal, vol. 23, pp. 28–41, (1978), Vekhande, C. et al.

Deutsch Gesundheitswes, vol. 22, pp. 1686–1688, (1967), Schmidt, G.

Primary Examiner—Benjamin R. Padgett
Assistant Examiner—M. Moskowitz
Attorney, Agent, or Firm—Hedmam, Casella, Gibson, Costigan & Hoare

[57] ABSTRACT

An improved colorimetric reagent is disclosed, which is adapted to the determination of the iron content in blood serum. The formulation comprises only two aqueous solutions: one of these comprises a buffer, a soluble salt of an alkali metal or an alkaline earth metal, Chromazurol B, a cationic or nonionic surfactant, whereas the other solution comprises a complexing agent and possibly the same ingredients of the chromogenic reagent for hindering the formation of the disturbing complex between chromazurol B, the surfactant and the iron: the complexing agent is a polycarboxylic acid or a salt thereof.

11 Claims, No Drawings

COMPOSITION FOR THE COLORIMETRIC DETERMINATION OF METALS

This invention relates to a colorimetric reagent which permits to detect the presence, in fluids of various nature, of metals which can exists in a number of oxidation states, and preferably of those metals which can become trivalent.

The colorimetric reagent the subject of this invention is particularly adapted to the quantitative determination of metals which are present in biological fluids and, among others, the iron in serum.

The present applicants are firmly convinced that the reagent to be described in more detail hereinafter finds quite a general field of use as far as the analyses of trivalent metals are concerned. However, the paramount importance of the specific sector of the diagnostics in biological fluids has induced the present applicants to restrict the examples, so that, for this reason, reference will be had, in the present specification, to the reagent adapted to detect the iron present in blood serum only and exclusively.

It will then be easy, for those skilled in the art, to extrapolate the definition of the reagent and its fields of use without departing from the scope of this invention.

The possibility is known of determining seral iron by using a number of chromogenic complexing agents, or by atomic absorption. The most widely used chromogenic complexing agents are:
  Sulphonated bathophenanthroline
  3-(2-pyridyl)-5,6-bis-(4-phenyl)sulfonic acid
  2,4,6-tripyridyl-s-triazine
  2,2'-dipyridyl, and others.

The methods which use such chromogenic agents provide, without exceptions, the setting free of the seral iron from transferrine, either by deproteination at acidic pH values, or by using specially provided capillary-active agents. The iron which has been set free from transferrine is then reduced to its ferrous state by strong reducing agents such as sodium dithionite, ascorbic acid, and others of the sort. The as-reduced iron is complexed by any of the chromogenic reagents listed above and forms colored complexes the extinction of which is proportional to the concentration of the iron in the sample being tested.

Recently, A. Garcic, in "Clin.Chim.Acta", 94, pages 115-119, (1979), has suggested a chromogenic agent which is extremely sensitive for the determination of the seral iron without deproteinizing the serum. The method described by this Author is based on the formation of a ternary complex between Chromazurole B (CAB), $Fe^{+++}/Fe^{++}$ and Cetyl-trimethylammonium bromide (CTMA).

Such complex has an absorption peak at 630 nm in a pH range of from 4.6 to 5.6.

The method is claimed to be linear up to 80 micromols Fe per liter and specific for dosing iron in serum.

The reagent suggested by the Author Garcic is comprised of the following solutions:

(A) - Buffer solution at pH 4.75, containing, in the final volume of one liter 25 g of anh.sodium acetate, 110 g of NaCl and 8 mls of glacial acetic acid;

(B) - Solution of Chromazurol B ammonium salt $2.10^{-3}$ mol per liter. In 100 mls of water are dissolved 0.1 g of Chromazurol B. The solution is declared to be stable for a month if stored in the dark;

(C) - Solution of cetyl trimethylammonium bromide $8.2 \cdot 10^{-3}$ mol per liter. In 100 mls of water are dissolved 0.3 g of cetyl trimethylammonium bromide.

One liter of reagent ready for use is obtained by admixing 850 mls of the solution (A) with 60 mls of the solution (B) and 90 mls of the solution (C). The solution is declared to remain stable for one month if stored in the dark.

Inasmuch as Chromazurol B reacts also with substances which are present in serum, the Author suggests, as a necessary precaution, the use of a masking solution comprised of:

Solution (D) (Masking): 17 g of monhydr.citric acid and 35 g of dihydr.sodium citrate in 100 mls of water. This solution has the task of complexing the iron of the blank sample to substract such iron from the CAB+CTMA couple.

Consequently, the Author suggests for metering the iron the following step sequence:

| | Sample | Standard | Blank Reag. | Blank sample | Blank Mask. |
|---|---|---|---|---|---|
| Serum, mls | 0.1 | * | * | 0.1 | * |
| Standard, mls | * | 0.1 | * | * | * |
| Dist. water, mls | * | * | 0.1 | * | 0.1 |
| Reag. ready f. use, mls | 3.0 | 3.0 | 3.0 | 3.0 | 3.0 |
| Masking soln., mls | * | * | * | 0.1 | 0.1 |

The samples, the standards and the reagents are admixed in test tubes in the quantities reported by the above Table. After 20 mins. readings are taken of the optical densities of the samples and of the standard against the blank reagent and the blank samples are read against the masking blank, at 630 nm wavelength. From the read out optical densities the concentration of iron in the sample can be reckoned.

We have found, and this is the subject matter of the present invention, a composition which permits to effect a novel formulation of a colorimetric reagent which is adapted, inter alia, to the determination of seral iron. This composition of ours is comprised of two solutions only, which preferably are aqueous solutions, ready for use: one acts as a chromogenic reagent for the iron in the sample, while the other solution is a masking reagent for the blank samples.

More particularly, the chromogenic reagent is comprised of a buffer, a soluble salt of an alkali metal (or an alkaline earth metal as the case may be), a soluble form of Chromazurol B (as such, or salified), a cationic surfactant (or a nonionic surfactant), and, in the case in which acid-form Chromazurol B is used, an additional solvent. In its turn, the masking reagent is comprised of the same components and, additionally, it contains a complexing agent which is capable of preventing the formation of the complex between Chromazurol B, the surfactant and the iron: such masking reagent might consist of the complexing agent alone. The various ingredients enumerated above can be present at various concentrations: as regards Chromazurol B, its quantity varies from 0.01 millimol per liter to 0.3 millimol per liter. The surfactant, in its turn, is added in amounts ranging from 0.1 to 400 times the quantity of Chromazurol B, as a function of its nature. The salt of the alkali metal, or the alkaline earth metal as the case may be, the task of which is to set free the iron from the transferrine, is added to the solution until a satisfactory result is achieved and, at any rate, in amounts over 0.004 mol per liter. The buffer, also consistently with its nature, is adopted in quantities ranging between 50 millimols/liter and 2 mols/liter, the pH being consequently varied between 4.5 and 5.6. Lastly, in the case of a supplementary solvent, the concentration thereof may range up to a top value of 30% of the volume of the solution.

As regards, now, the masking solution, the complexing agent which inhibits the formation of the complex between chromazurol B, the surfactant and the iron, is added in amonts which are varied consistently with its nature and its complexing power and, anyhow, in molar amounts not below those of chromazurol B.

Among all the possible ingredients, the soluble salt is, preferably, a magnesium salt and, among others, a halide. The Chromazurol B, as outlined above, can be present as such: if so, it requires an additional solvent such as ethanol. The surfactant is selected from among the alkylammonium halides, such as cetyl trimethylammonium bromide, or, as an alternative, from among the polyhydroxyalkylene ethers. The complexing agent which is present in the masking reagent is selected, in its turn, from among the polycarboxylic organic acids and their salts; by way of example, it can be monohydrate citric acid and bihydrate tribasic sodium citrate.

A standard formulation according to the present invention is as follows:

(I) CHROMOGENIC REAGENT

Acetic-acid/NaOH buffer pH 4.75, 0.5 M: $MgCl_2.6H_2O$: 60 g/liter
CAB: 70 mg/liter (acidic CAB)
CTMA: 270 mg/liter
95%-ethanol: 100 mls/liter

(II) MASKING REAGENT

The concentrations of the several ingredients of the Chromogenic Reagent remain unaltered for the Masking Reagent.
Further ingredients which are present are:
Monohydrate citric acid: 5.48 g/liter
Bihydrate tribasic sodium citrate: 11.29 g/liter The solutions, stored in the dark between 0° C. and 37° C. have a stability which by far exceeds that of the known reagent and, very presumably, they retain their activity unaltered for periods of one year and perhaps more.

The analytical method based on the use of the formulation according to the present invention does not substantially differ from that suggested by Garcic, but affords an advantage with respect thereto, since it is no longer necessary to add to the reagent ready for use the masking solution D.

This fact is an asset in the analytical routine since the number of manipulative operations is reduced, and there is also an advantage from the theoretical standpoint inasmuch as the volume of the reaction mixture is exactly the same as that of the blank mixture.

For the sake of clarity, the proposed reaction pattern is set forth hereunder:

|  | Sample | Standard | Blank Reagt. | Blank sample | Blank Mask. |
|---|---|---|---|---|---|
| Serum, mls | 0.1 | * | * | 0.1 | * |
| Standard, mls | * | 0.1 | * | * | 0.1 |
| Dist. water, mls | * | * | 0.1 | * | * |
| Chromogenic Rgt., mls (I) | 2.0 | 2.0 | 2.0 | * | * |
| Masking Rgt. (II), mls | * | * | * | 2.0 | 2.0 |

Incubation is for 20 mins. at 37° C. and readings taken at 640 nm wavelength.

EXAMPLE 1

By utilizing a composition corresponding to the standard formulation reported hereinabove, a set of tests have been conducted to ascertain the characteristics of the composition under test.

(1) Accuracy test

By adding progressive quantities, known, of $Fe^{+++}$ to a serum, an ave.recovery of 102.7% linear between 0 and 100 micrograms per 100 mls of added iron has been recorded. This fact means that the iron which was present in the serum had slightly been overdosed, but the error had nevertheless been negligible, as evidenced by the correlation coefficient between the quantity of iron introduced and the quantity of iron found was as high as 0.998.

(2) Linearity test

The correlation between the extinction at 640 nm and the iron concentration was linear up to a conc. of 480 micrograms per 100 mls of sample, of iron.

(3) Comparative test

The reagent of this invention has been compared with a commercial kit based on the use, as the chromogenic agent, of the sulfonated bathophenanthroline and has given, on 33 samples of human blood serum, the following results:

y (comparison) = 0.93x(invention)
6.17 micrograms/100 mls with correlation coefficient, r, equal to 0.98.

EXAMPLE 2

By still using a composition corresponding to the standard formulation of this invention, its stability in time has been tested by checking the optical density of the reagent and its useability with control solutions and sera having a known iron content. The reagent, during the entire check period, has been stored sheltered from direct light and at three different temperatures, viz. 4° C., 20° C. and 37° C.

On completion of the check period, which last 80 days, the reagent did not show any variations in its optical density, or reactivity losses, and retained its initial properties unaltered, that which leads to forecast the possibility of long storage times without any decay.

TABLE 1

OPTICAL DENSITY - 640 nm wavelength, in time

| Number of days | 0 | 20 | 40 | 60 | 80 |
|---|---|---|---|---|---|
| Chromogen. Reag. | 0.175 | 0.173 | 0.175 | 0.177 | 0.176 |
| Masking Reagent | 0.116 | 0.114 | 0.115 | 0.114 | 0.115 |

TABLE 2

DOSAGE OF A STAND. SOLN. OF 100 MICROGRAMS PER 100 MLS OF $Fe^{+++}$, AND OF A CONTROL SERUM HAVING A TITLE EQUAL TO 98 MICROGRAMS OF $Fe^{+++}$ PER 100 MLS.

| Number of days | 0 | 20 | 40 | 60 | 80 |
|---|---|---|---|---|---|
| Opt. Dens. 640 nm |  |  |  |  |  |

TABLE 2-continued

DOSAGE OF A STAND. SOLN. OF 100 MICROGRAMS PER 100 MLS OF $Fe^{+++}$, AND OF A CONTROL SERUM HAVING A TITLE EQUAL TO 98 MICROGRAMS OF $Fe^{+++}$ PER 100 MLS.

| Number of days | 0 | 20 | 40 | 60 | 80 |
|---|---|---|---|---|---|
| Standard Soln. | 0.110 | 0.108 | 0.105 | 0.106 | 0.110 |
| Control serum micrograms/100 ml | 98 | 97 | 102 | 99 | 97 |

We claim:

1. A diagnostic kit for a colorimetric reagent adapted to the determination of the iron content in blood serum, consisting of two solutions only, the former containing a buffer, a soluble salt of a metal selected from the group comprising the alkali metals and the alkaline earth metals, a soluble form of Chromazurol B, a cationic surface-active agent or a nonionic surface-active agent, the latter solution containing a complexing agent capable of hindering the formation of a complex between the Chromazurol B, the surface-active agent and the iron with the same ingredients of the former solution.

2. A diagnostic kit for a colorimetric reagent according to claim 1, wherein the former solution contains a salified form of Chromazurol B.

3. A diagnostic kit for a colorimetric reagent according to claim 1, wherein the former solution contains Chromazurol B in acid-form and an additional solvent.

4. A diagnostic kit for a colorimetric reagent according to claim 3, wherein the former solution contains acid-form Chromazurol B and, additionally, ethanol.

5. A diagnostic kit for a colorimetric reagent according to claim 3, wherein the former solution consists of a buffer, a magnesium halide, acid-form Chromazurol B, ethanol and cetyl trimethylammonium bromide.

6. A diagnostic kit for a colorimetric reagent according to claim 5, wherein the latter solution additionally contains monohydrate citric acid and bihhydrate tribasic sodium citrate.

7. A method for the determination of the iron content of blood serum which comprises:
   (a) combining a sample of serum with a chromogenic reagent which comprises a buffer; a soluble salt of a metal selected from the group consisting of the alkali metals and alkaline earth metals; a soluble form of Chromazurol B; and a cationic surface-active agent or a nonionic surface-active agent to form a test sample;
   (b) combining a sample of serum with a masking reagent which comprises a buffer, a soluble salt of a metal selected from the group consisting of the alkali metals and alkaline earth metals; a soluble form of Chromazurol B; a cationic surface-active agent or a nonionic surface-active agent; and a complexing agent capable of hindering the formation of a complex between the Chromazurol B and iron to form a blank sample;
   (c) combining a standard with the chromogenic agent of step (a) to form a test standard;
   (d) combining distilled water with the chromogenic reagent of step (a) to form a blank reagent;
   (e) combining the masking reagent of step (b) with the standard to form a masking blank of step (b);
   (f) determining the optical density of each of the materials from steps (a), (b), (c), (d), and (e) in a colorimeter;
   (g) comparing the optical density of the test sample with the test standard after allowance is taken for the optical density of the blank reagent, the blank sample, and the masking blank to determine the amount of iron that is present.

8. A method as defined in claim 7 wherein the salt of a metal is magnesium chloride.

9. A method as defined in claim 8 wherein each of steps (a), (b), (c), (d), and (e) is carried out with an amount of materials that gives an equal volume of blank sample, test standard, blank sample, masking blank, and blank reagent.

10. A composition as defined in claim 5 wherein the magnesium halide is magnesium chloride.

11. A masking composition for use in determining iron, said composition comprising a buffer; a soluble salt of a metal selected from the group consisting of the alkali metals, and alkaline earth metals; a soluble form of Chromazurol B; a cationic surface-active agent; or a nonionic surface-active agent; a complexing agent capable of hindering the formation of a complex between the Chromazurol B and iron.

* * * * *